US006620850B2

(12) United States Patent
Martynyuk et al.

(10) Patent No.: US 6,620,850 B2
(45) Date of Patent: Sep. 16, 2003

(54) MATERIALS AND METHODS FOR TREATMENT OF NEUROLOGICAL DISORDERS INVOLVING OVERACTIVATION OF GLUTAMATERGIC IONOTROPIC RECEPTORS

(75) Inventors: Anatoly E. Martynyuk, Gainesville, FL (US); Donn Michael Dennis, Gainesville, FL (US); Alexander V. Glushakov, Gainesville, FL (US); Colin Sumners, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/957,358

(22) Filed: Sep. 19, 2001

(65) Prior Publication Data

US 2003/0055099 A1 Mar. 20, 2003

(51) Int. Cl.⁷ .............................................. A61K 31/198
(52) U.S. Cl. ....................................... 514/567; 514/419
(58) Field of Search ................................ 514/561, 567, 514/419

(56) References Cited

U.S. PATENT DOCUMENTS

| | | | |
|---|---|---|---|
| 4,279,917 A | 7/1981 | Takami et al. ............... | 424/273 |
| 4,491,589 A | 1/1985 | Dell et al. ................... | 424/274 |
| 4,604,286 A | 8/1986 | Kawajiri ...................... | 424/149 |
| 5,089,517 A | 2/1992 | Choi et al. ................... | 514/411 |
| 5,447,948 A | 9/1995 | Seibyl et al. ................ | 514/393 |
| 5,605,818 A | 2/1997 | Katsumata et al. .......... | 435/108 |
| 5,670,539 A * | 9/1997 | Richardson .................. | 514/561 |
| 5,789,444 A | 8/1998 | Choi et al. ................... | 514/567 |
| 6,001,575 A | 12/1999 | Huganir et al. ................ | 435/6 |
| 6,013,672 A | 1/2000 | Ye et al. ....................... | 514/561 |
| 6,084,084 A | 7/2000 | Stormann et al. ........... | 536/23.5 |
| 6,362,226 B2 | 3/2002 | Phillips, III et al. ......... | 514/568 |

OTHER PUBLICATIONS

Belardinelli, L. et al. "1,3–Dipropyl–8–[2–(5,6–Epoxy)Norbornyl]Xanthine, a Potent, Specific and Selective $A_1$ Adenosine Receptor Antagonist in the Guinea Pig Heart and Brain and in DDT₁MF–2 Cells" *J. Pharmacol. Exp. Ther.*, 1995, 275(3):1167–1176.

Choi, D.W. "Excitotoxic Cell Death" *J. Neurobiol.*, 1992, 23(9):1261–1276.

Dennis, D.M. et al. "Homologous Desensitization of the $A_1$–Adenosine Receptor System in the Guinea Pig Atrioventricular Node" *J. Pharmacol. Exp. Ther.*, 1995, 272(3):1024–1035.

Kostyuk, P.G. et al. "Effects of intracellular administration of L–tyrosine and L–phenylalanine on voltage–operated calcium conductance in PC12 pheochromocytoma cells" *Brain Res.*, 1991, 550:11–14.

Krystal, J.H. et al. "NMDA Agonists and Antagonist as Probes of Glutamatergic Dysfunction and Pharmacotherapies in Neuropsychiatric Disorders" *Harv. Rev. Psyschiatry*, Sep.–Oct. 1999, 7(3):125–143.

Lipton, S.A. and P.A. Rosenberg "Excitatory Amino Acids as a Final Common Pathway for Neurologic Disorders" *N. Engl. J. Med.*, 1994, 330(9):613–622.

Martynyuk, A.E. et al. "Blocking effect of intraperitoneal injection of phenylalanine on high–threshold calcium currents in rat hippocampal neurons" *Brain Res.*, 1991, 552:228–231.

Martynyuk, A.E. et al. "Adenosine increases potassium conductance in isolated rabbit atriventricular nodal myocytes" *Cardiovasc. Res.* 1995, 30:668–675.

Martynyuk, A.E. et al. "Hyperkalemia Enhances the Effect of Adenosine on $I_{K,ADO}$ in Rabbit Isolated AV Nodal Myocytes and on AV Nodal Conduction in Guinea Pig Isolated Heart" *Circulation*, 1999, 99:312–318.

Morey, T.E. et al. "Structure–Activity Relationships and Electrophysiological Effects of Short–Acting Amiodarone Homologs in Guinea Pig Isolated Heart" *J. Pharmacol. Exp. Ther.*, 2001, 297(1):260–266.

Morey, T.E. et al. "Ionic Basis of the Differential Effects of Intravenous Anesthetics on Erythromycin–induced Prolongation of Ventricular Repolarization in the Guinea Pig Heart" *Anesthesiology*, 1997, 87:1172–1181.

Seubert, C.N. et al. "Midazolam Selectively Potentiates the $A_{2A}$–but not $A_1$–receptor–mediated Effects of Adenosine" *Anesthesiology*, 2000, 92:567–577.

Tanaka, H. et al. "The AMPAR subunit GluR2: still front and center–stage" *Brain Res.*, 2000, 886:190–207.

Weiss, J.H. and S.L. Sensi "$Ca^{2+}$—$Zn^{2+}$ permeable AMPA or kainite receptors: possible key factors in selective neurodegeneration" *Trends Neurosci.*, 2000, 23(8)365–371.

Zima, A. et al. "Antagonism of the Positive Dromotropic Effects of Isopoterenol by Adenosine: Role of Nitric Oxide, cGMP–dependent camp–phosphodiesterase and Protein Kinase G" *J. Mol. Cell. Cardiol.*, 2000, 32:1609–1619.

Chiaroni, P. et al. "A multvariate analysis of red blood cell membrane transports and plasma levels of L–Tyrosine and L–Tryptophan in depressed patients before treatment and after clinical improvement" *Neuropsychobiology*, 1990, 23:1–7.

Dollins, A.B. et al. "L–Tyrosine ameliorates some effects of lower body negative pressure stress" *Physiology & Behavior*, 1995, 57(2):223–230.

Eaton, S.A. et al. "Competitive antagonism at metabotropic glutamate receptors (S)–4–carboxyphenylglycine and (RS)–α–methyl–4–carboxyphenylglycine" *European Journal of Pharmacology–Molecular Pharmacology Section*, 1993, 244:195–197.

(List continued on next page.)

*Primary Examiner*—Phyllis G. Spivack
(74) *Attorney, Agent, or Firm*—Saliwanchik, Lloyd & Saliwanchik

(57) ABSTRACT

The subject invention pertains to methods for treatment of neurological conditions related to, or which can be affected by, modulation of glutamate receptor (GluR) activity. The treatment can be either prophylactic in nature or to alleviate symptoms of such neurological conditions as ischemia, stroke, spinal cord injury and traumatic brain injury.

26 Claims, 5 Drawing Sheets

OTHER PUBLICATIONS

Gagliardi, R.J. "Neuroprotection, excitotoxicicity and NMDA antagonists" *Arq. Neuropsiquiatr*, 2000, 58(2–B):583–588.

Galloway, G.P. et al. "A historically controlled trial of tyrosine for cocaine dependence" *Journal of Psychoactive Drugs*, Jul.–Sep. 1996, 28(3):305–309.

Gelenberg, A.J. et al. "Neurotransmitter percursors for the treatment of depression" *Psychopharmacology Bulletin*, Jan. 1982, 18(1):7–18.

Hajak, G. et al. "The influence of intravenous L–Tryptophan on plasma melatonin and sleep in men" *Pharmacopsychiat.*, 1991, 24:17–20.

Heller, B. et al. "Therapeutic action of D–phenylalanine in Parkinson's Disease" *Arzneim.–Forsch (Drug Res.)*, 1976, 26(4):577–579.

Hollman, M. et al. "Cloned Glutamate Receptors" *Annu. Rev. Neurosci.*, 1994, 17:31–108.

Knopfel, T. et al. "Metabotropic glutamate receptors: Novel targets for drug development"*Journal of Medicinal Chemistry*, Apr. 1995, 38(9):1417–1426.

Maiese, K. et al. "Group I and Group II metabotropic glutamate receptor subtypes provide enhanced neuroprotection" *Journal of Neuroscience Research*, 2000, 62:257–272.

Meyer, J.S. et al. "Neurotransmitter precursor amino acids in the treatment of multi–infarct Dementia and Alzheimer's Disease" *Journal of the American Geriatrics Society*, Jul. 1977, 25(7)289–298.

Obrenovitch, T.P. "Excitotoxicity in neurological disorders—the glutamate paradox", *Int. J. Devl. Neuroscience*, 2000, 18:281–287.

Sapolsky, R.M. "Cellular defenses against excitotoxic insults" *Journal of Neurochemistry*, 2001, 76:1601–1611.

Schoepp, D.D. et al. "Metabotropic glutamate receptors in brain function and pathology" TiPS, Jan. 1993, 14:13–20.

Sekiyama, N. et al. "Structure–activity relationships of new agonists and antagonists of different metabotropic glutamate receptor subtypes"*British Journal of Pharmacology*, 1996, 117:1493–1503.

Watkins, J. et al. "Phenylglycine derivatives as antagonists of metabotropic glutamate receptors" TiPS, Sep. 1994, 15:333–342.

Zipfel, G.J. et al. "Neuronal apoptosis after CNS injury: The roles of glutamate and calcium" *Journal of Neurotrauma*, 2000, 17(10):857–869.

* cited by examiner

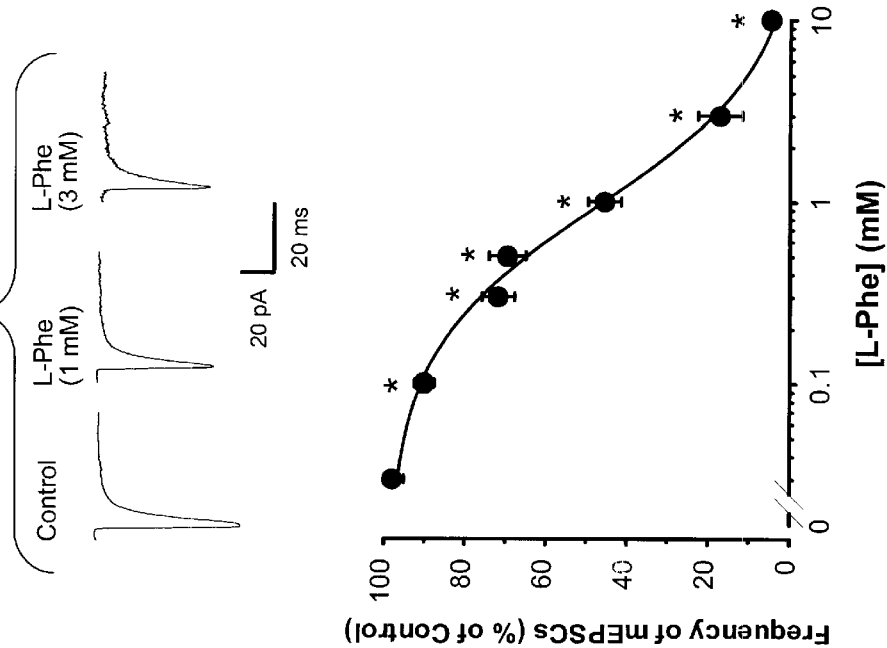
FIG. 1B
FIG. 1C
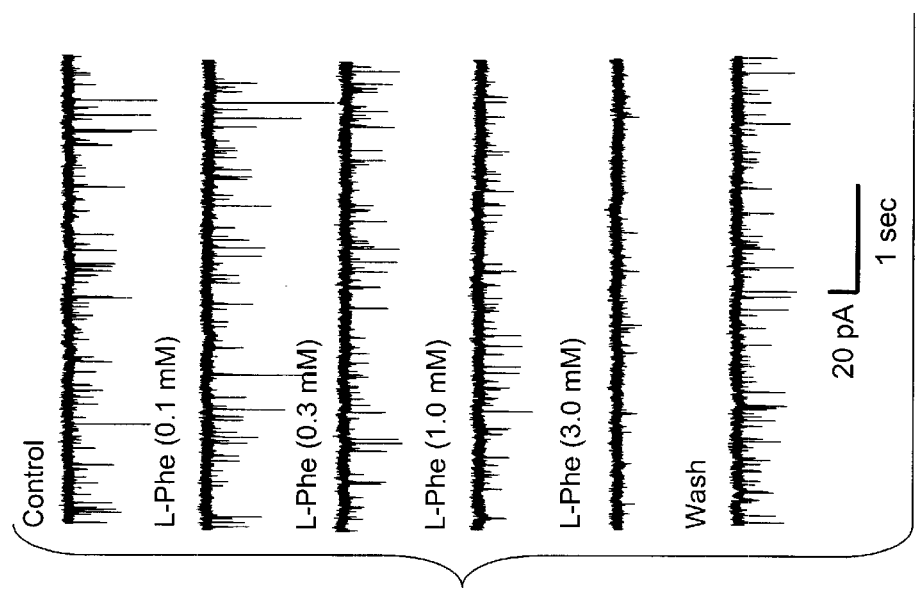
FIG. 1A

MATERIALS AND METHODS FOR TREATMENT OF NEUROLOGICAL DISORDERS INVOLVING OVERACTIVATION OF GLUTAMATERGIC IONOTROPIC RECEPTORS

BACKGROUND OF THE INVENTION

Glutamate is the principal excitatory neurotransmitter in the mammalian brain and is known to participate in higher order processes, such as development, learning, and memory. As an excitatory amino acid (EAA), glutamate is also involved in neuropathologic events, including cell death, that result from excessive stimulation of post-synaptic neurons (i.e., excitotoxic damage). Glutamate binds or interacts with one or more glutamate receptors (GluRs), which can be differentiated pharmacologically into different classes and subtypes. In the mammalian central nervous system (CNS) there are three main subtypes of ionotropic glutamate receptors (iGluRs), defined pharmacologically by the selective agonists N-methyl-D-aspartate (NMDA), kainite (KA), and α-amino-3-hydroxyl-5-methly-4-isoxazolepropionic acid (AMPA).

The iGluRs are ligand-gated ion channels that, upon binding glutamate, open to allow the selective influx of certain monovalent and divalent cations, thereby depolarizing the cell membrane. In addition, certain iGluRs with relatively high calcium permeability can activate a variety of calcium-dependent intracellular processes.

During a period of anoxia (e.g., cardiopulmonary resuscitation), ischemic stroke, epileptic seizure, and other types of CNS injury, GluRs of the NMDA, KA, and AMPA subtypes are overactivated (Choi D W [1992] Nuerobiol 9:1261–96; Zipfel G J et al., [2000] J Neurotrauma 10:857–69; Fountain N B. [2000] Epilesia 41 Suppl 2:S23–30; Tanaka H et al. [2000] Brain Res 886(1–2):190–207; Pujol R et al. [1999] Ann NY Acad Sci 884:249–254). The net result of this effect is a massive increase in the concentration of intracellular calcium, which in turn triggers a deleterious cascade of events leading to neuronal death (Sapolsky R M [2001] J Neurochem 76(6):1601–1611). Functional overactivity of iGluRs has also been implicated in a variety of neurodegenerative diseases, such as lateral sclerosis, Alzheimer's disease, Huntington's chorea and AIDS dementia syndrome (Tanaka H et al. [2000] Brain Res 886(1–2):190–207).

In the search for safe and efficacious neuroprotective agents, iGluR antagonists remain thought of as promising therapeutic drugs (Gagliardi R J [2000] Arq Neuropsiquiatr 58(2B):583–588). A minimum of 800 neuroprotective trials using GluR antagonists is currently underway worldwide. Among the neuroprotective agents being studied, the most important ones include iGluR antagonists of the NMDA and AMPA subtype, and inhibitors of glutamate release. However, many of these drugs cause significant side effects (e.g., neurotoxicity) that will probably limit their widespread clinical use. For example, the NMDA channel blocker dizocilpine (MK-801) causes neuronal vacuolation in specific areas of the rat brain cortex (Olney J W et al. [1989] Science 244:1360–1362; Fix A S et al. [1994] Drug Development Research 32:147–152; Muir K W et al. [1995] Stroke 26:503–513).

In contrast to the iGluRs, the metabotropic glutamate receptors (mGluRs) are G protein-coupled receptors capable of activating a variety of intracellular second messenger systems following the binding of glutamate. Activation of mGluRs in mammalian neurons can decrease the activity of ion channels, including ligand-gated channels such as iGluRs. Several subtypes of mGluRs have been isolated by molecular cloning. In addition, the various subtypes of mGluRs have been divided into three groups based on amino acid sequence homologies, the second messenger systems they utilize, and pharmacological characteristics (Nakanishi [1994] Neuron 13:1031).

U.S. Pat. No. 6,084,084 (the '084 patent) discloses a human mGluR protein and methods of screening for compounds that bind to the mGluR receptor and modulate its activity, and using such compounds to treat various neurological disorders. The '084 patent also cites several references that teach various mGluR modulators, the majority of which are L-glutamate derivatives.

A family of substances that have not previously been investigated as modulators of GluR activity are the naturally occurring aromatic amino acids, L-tyrosine, L-tryptophan, and L-phenylalanine. While some phenylalanine derivatives have been investigated as possible agonists or antagonists of mGluR activity, these derivatives showed little or no agonist or antagonist activity on any subtypes of the receptors investigated (Sekiyama N et al. [1996] Br J Pharmacol 117:1493–1503).

Aromatic amino acids have been available as over-the-counter dietary supplements for some time, with their consumption generally viewed as beneficial for their role as biosynthetic precursors for the neurotransmitter precursors serotonin, dopamine, and norepinephrine. In addition, there is research suggesting that oral administration of neurotransmitter precursors may be useful in treatment of some pathologic conditions of the brain, but not others. For example, oral administration of preparations that included tyrosine was found to confer some benefit to patients suffering from multi-infarct dementia and Alzheimer's disease (Meyer J S et al. [1977] J Am Geriatr Soc (July) 25(7):289–298), and oral administration of D-phenylalanine conferred some benefit on patients suffering from Parkinson's disease (Heller B et al. [1976] Arzheim-Forsch (Drug Res.) 26(4):577–579); however, orally administered tyrosine did not confer a benefit to patients suffering from cocaine dependence (Galloway G P et al. [1996] J Psychoactive Drugs (July–September) 28(3):305–309).

It is evident that the currently available glutamate receptor modulators may be of limited use, both as research tools and potential therapeutic agents, as a result of their lack of potency and selectivity. Accordingly, there remains a need for safe and efficacious neuroprotective agents.

BRIEF SUMMARY OF THE INVENTION

The subject invention concerns methods for treating a disease or condition which is related to, or which can be affected by, modulation of glutamate receptor (GluR) activity. Particularly, the subject invention concerns methods for treating neurological conditions characterized by excessive activation of glutamatergic ionotropic receptors (iGluR). The treatment can be either prophylactic in nature or to alleviate symptoms of such neurological conditions.

According to the methods of the subject invention, an AAA is administered in an amount effective to increase the concentration of the AAA within the brain to a level above physiologically normal. For example, the AAA can be administered in an amount effective to bring the patient's AAA blood plasma level within the range of about 200 $\mu$M to about 2000 $\mu$M. Preferably, the patient's AAA blood plasma level is brought to within the range of about 300 $\mu$M to about 1800 μM. More preferably, the patient's AAA plasma level is brought to within the range of about 800 μM to about 1500 μM. However, the appropriate concentration of AAAs in the blood can be adjusted, as permeability of the blood-brain barrier can vary with different disease states.

Neurological conditions characterized by excessive activation of glutamatergic ionotropic receptors (iGluRs) include, but are not limited to, anoxic/hypoxic damage (e.g., cardiopulmonary resuscitation, drowning), traumatic brain injury, spinal cord injury, local anesthetic-induced seizure activity, ischemic stroke, ischemic neurodegeneration of the retina, epilepticus, Tourette's syndrome, obsessive-compulsive disorder, drug-induced (e.g., nerve gas-induced) CNS injury, chronic pain syndromes, acute and chronic neurodegenerative disorders (e.g., lateral sclerosis, Alzheimer's disease, Huntington's chorea), AIDS dementia syndrome, cocaine addiction, or combinations thereof. In one embodiment, the method of the subject invention comprises parenterally administering to the patient an AAA, an analog or isomer of an AAA, or combinations thereof.

Unless otherwise indicated, as used herein, the term "AAA" includes naturally occurring aromatic amino acids (e.g., L-tyrosine, L-phenylalanine, and L-tryptophan), their isomers, including optical isomers (e.g., dextrorotatory (D-), levorotatory (L-), or mixtures (DL-) thereof), and analogs thereof. Mixtures of naturally occurring aromatic amino acids, isomers, and analogs, are also contemplated.

The present invention also concerns methods for modulating GluR activity. In one aspect, the method of the subject invention comprises lowering Glu concentration in the synaptic cleft in a patient by administering an AAA. The present invention further pertains to methods for attenuating GluR-mediated miniature excitatory postsynaptic currents (mEPSCs), either during normoxia or ischemic conditions, within a patient by administering an AAA. In addition, the present invention concerns methods for inhibiting GluR activity in a patient by lowering the concentration of Glu in a patient through the administration of an AAA.

The subject invention also concerns articles of manufacture useful in treating a neurological condition characterized by overactivation of an ionotropic glutamatergic receptor.

BRIEF DESCRIPTION OF THE DRAWINGS

FIGS. 1A–1C show the effect of L-Phe on mEPSCs in rat cultured hippocampal neurons. Examples of mEPSCs, recorded in the presence of the NMDA channel blocker MK-801 before, during, and after application of L-Phe are shown in FIG. 1A. FIG. 1B shows an example of averaged mEPSCs recorded from the same neuron shown in FIG. 1A. FIG. 1C shows the concentration-dependence of attenuation of the frequency of mEPSCs caused by L-Phe. The frequencies of mEPSCs were normalized to control values and plotted against the concentration of L-Phe. The data are expressed as mean±S.E.M. for 5 to 8 cells. *, P<0.01 compared to control. Some error bars fell with the radius of a symbol.

FIG. 2B shows summary data for 5–8 experiments demonstrating the effect of L-Tyr, L-Trp, and L-Phe on the frequency of mEPSCs. The frequencies of events were normalized to control values and plotted against the concentration of L-Tyr, L-Trp, and L-Phe. The results are presented as mean±S.E.M. *, P<0.01 compared to control.

FIG. 3B shows an example of averaged mEPSCs recorded from the same neuron shown in FIG. 3A. FIG. 3C shows summary data for four experiments demonstrating the effect of L-Phe on the frequency of mEPSCs. The frequency of mEPSCs during ED was taken as 100%. *, P<0.01 compared to the values of frequency of mEPSCs during ED only.

FIG. 4B shows summary data for 5–8 experiments demonstrating the effect of D-Tyr, D-Trp, and D-Phe on the frequency of mEPSCs. The frequencies of mEPSCs were normalized to control values and plotted against the concentration of D-Tyr, D-Trp, and D-Phe. The results are presented as means±S.E.M. *, P<0.01 compared to control.

DETAILED DISCLOSURE OF THE INVENTION

Figures 2A, 2B:
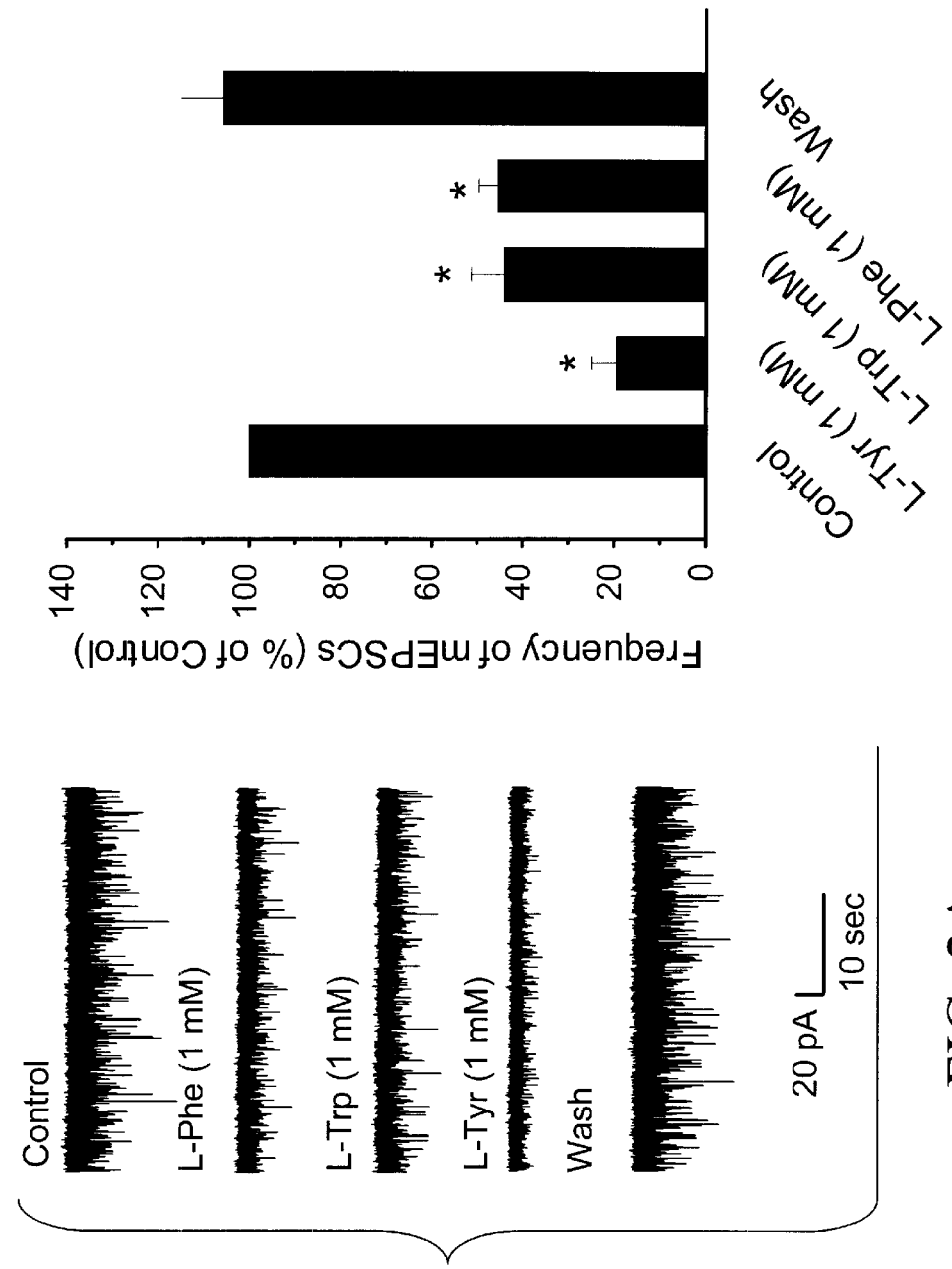
FIGS. 2A and 2B show the effect of L-tyrosine, L-phenylalanine, and L-tryptophan on the frequency of mEPSCs in rat cultured hippocampal neurons. Examples of mEPSCs, recorded in the presence of the NMDA channel blocker MK-801 before, during, and after application of L-tyrosine (L-Tyr), L-phenylalanine (L-Phe), or L-Tryptophan (L-Trp) are shown in FIG. 2A.

The subject invention concerns methods for treating a neurological condition which is related to, or which can be affected by, modulation of glutamate receptor (GluR) activity. The treatment can be either prophylactic in nature or to alleviate symptoms of such neurological conditions.

Particularly, the subject invention concerns methods for treating neurological conditions characterized by excessive activation of glutamatergic ionotropic receptors (iGluR). Neurological conditions characterized by excessive activation of glutamatergic ionotropic receptors (iGluRs) include, but are not limited to, anoxic/hypoxic damage (e.g., cardiopulmonary resuscitation, drowning), traumatic brain injury, spinal cord injury, local anesthetic-induced seizure activity, ischemic stroke, ischemic neurodegeneration of the retina, epilepticus, Tourette's syndrome, obsessive-compulsive disorder, drug-induced (e.g., nerve gas-induced) CNS injury, chronic pain syndromes, acute and chronic neurodegenerative disorders (e.g., lateral sclerosis, Alzheimer's disease, Huntington's chorea), AIDS dementia syndrome, cocaine addiction, or combinations thereof. In one embodiment, the method of the subject invention comprises parenterally administering one or more AAAs to a patient.

Unless otherwise indicated, as used herein, the term "AAA" includes naturally occurring aromatic amino acids (e.g., L-tyrosine, L-phenylalanine, and L-tryptophan), their isomers, including optical isomers (e.g., dextrorotatory (D-), levorotatory (L-), or mixtures thereof (DL-)), and analogs thereof. Mixtures of naturally occurring aromatic amino acids, isomers, and analogs are also contemplated. Examples of mixtures of the naturally occurring aromatic amino acids include, but are not limited to L-tyrosine and L-tryptophan;

L-tyrosine and L-phenylalanine; L-tryptophan and L-phenylalanine; and L-tyrosine, L-tryptophan, and L-phenylalanine. Each of the naturally occurring amino acids in these mixtures can be substituted with an isomer or analog.

In a preferred embodiment, the subject invention involves treating a patient suffering from a neurological condition characterized by excessive activation of iGluRs. Also in a preferred embodiment, the AAA has an effect on a physiological or pathophysiological activity. By way of illustration, and not limitation, these activities can include convulsions, neuroprotection, neuronal death, neuronal development, central control of cardiac activity, waking, motor control, and control of vestibo ocular reflex. In another embodiment, the method of the subject invention further comprises diagnosis and/or monitoring of a neurological condition within the patient, wherein the condition is characterized by excessive activation of iGluRs.

The subject invention is at least partly based on the observation that aromatic amino acids (AAAs) (L- and D-forms of phenylalanine, tyrosine, and tryptophan) diminish iGluR-mediated mEPSCs in cultured rat hippocampal neurons. The AAAs significantly diminished control mEPSCs during normoxia and significantly diminished mEPSCs which were augmented during ischemic insult (energy deprivation). To induce energy deprivation, glucose was replaced with 2 mM 2-deoxyglucose, and 5 mM sodium cyanide (NaCN) was added. Without being limited by theory, the experimental results suggest that the inhibition of GluR-mediated synaptic transmission occurs due to a decrease of Glu concentration in the synaptic cleft. AAAs may decrease concentration of Glu by one or more of the following: (1) activation of receptors which inhibit Glu release presynaptically, such as metabrotropic GluRs (mGluRs), $M_2$ muscarinic, $\alpha_2$-adrenergic and $\gamma$-aminobutyric acid subtype B ($GABA_B$) receptors; (2) inhibition of the vesicular release machinery of Glu; or (3) stimulation of Glu uptake.

In accordance with the subject invention, an AAA can be administered to a patient through a variety of parenteral routes. For example, an AAA can be administered to the patient intravenously or nasally. Alternatively, an AAA can be administered directly into the patient's brain, through microdialysis techniques, for example.

Figure 5:
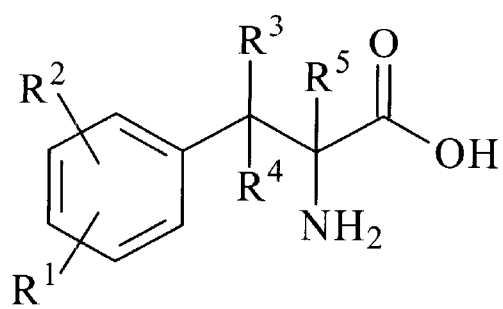
FIGS. 5–7 show formulas representing AAA analogs of the subject invention.
Figure 6:
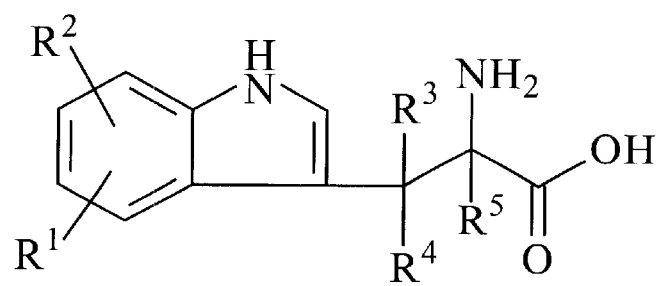
Figure 7:
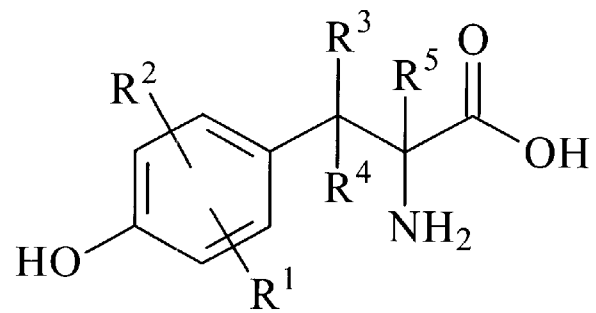

AAA analogs of the subject invention include analogs of naturally occurring AAAs and analogs of their isomers. Analogs of the subject invention can be substituted at various positions. FIGS. 5–7 show formulas representing AAA analogs of the subject invention. It should be understood that while the AAA analogs of the subject invention can be produced by modifying the naturally occurring aromatic amino acids (phenylalanine, tryptophan, and tyrosine), it is contemplated that other starting materials (e.g., other amino acids) can be utilized to produce the AAA analogs of the subject invention, using methods of organic synthesis known to those skilled in the art.

Referring now to each of the formulas in FIGS. 5 through 7, $R^1$ and $R^2$, which may be the same or different, can be H, alkyl, alkenyl, alkynyl, halogen, or alkoxy. $R^3$ can be H, O, alkyl, alkenyl, alkynyl, halogen, or alkoxy. $R^4$ can be H, alkyl, alkenyl, alkynyl, halogen, or alkoxy, but is not present when $R^3$ is O. $R^5$ can be H, alkyl, alkenyl, alkynyl, halogen, or alkoxy.

In one embodiment, in the formulas shown in FIG. 5 and FIG. 7, the pair of substituents, $R^3$ and $R^4$, can together form a cyclic group, wherein the resulting ring structure is selected from the group consisting of cycloalkyl, cycloalkenyl, heterocycloalkyl, heterocycloalkenyl, aryl, and heteroaryl. The resulting ring structure can optionally be benzofused at any available position.

As used in the specification, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tert-butyl, pentyl, hexyl, octyl, and the like. In another embodiment, the alkyl moiety is $C_{1-3}$ alkyl.

The term "alkenyl" refers to a straight or branched chain alkyl moiety having in addition one or more carbon—carbon double bonds, of either E or Z stereochemistry where applicable. In one embodiment, the alkenyl moiety is $C_{2-6}$ alkenyl, which refers to an alkenyl moiety having two to six carbon atoms. This term would include, for example, vinyl, 1-propenyl, 1- and 2-butenyl, 2-methyl-2-propenyl, and the like.

The term "alkynyl" refers to a straight or branched chain alkyl moiety having in addition one or more carbon—carbon triple bonds. In one embodiment, the alkynyl moiety is $C_{2-6}$ alkynyl, which refers to an alkynyl moiety having two to six carbon atoms. This term would include, for example, ethynyl, 1-propynyl, 1- and 2-butynyl, 1-methyl-2-butynyl, and the like.

The term "alkoxy" refers to an alkyl-O-group, in which the alky group is as previously described.

The term "halogen" refers to fluorine, chlorine, bromine, or iodine.

The term "cycloalkenyl" refers to an alicyclic moiety having from three to six carbon atoms and having in addition one double bond. This term includes, for example, cyclopentenyl and cyclohexenyl.

The term "heterocycloalkyl" refers to a saturated heterocyclic moiety having from two to six carbon atoms and one or more heteroatom from the group N, O, S (or oxidized versions thereof) which may be optionally benzofused at any available position. This includes for example azetidinyl, pyrrolidinyl, tetrahydrofuranyl, piperidinyl, benzodioxole and the like.

The term "heterocycloalkenyl" refers to an alicyclic moiety having from three to six carbon atoms and one or more heteroatoms from the group N, O, S and having in addition one double bond. This term includes, for example, dihydropyranyl.

The term "aryl" refers to an aromatic carbocyclic ring, optionally substituted with, or fused with, an aryl group. This term includes, for example phenyl or naphthyl.

The term "heteroaryl" refers to aromatic ring systems of five to ten atoms of which at least one atom is selected from O, N, and S, and optionally substituted with an aryl group substituent. This term includes for example furanyl, thiophenyl, pyridyl, indolyl, quinolyl and the like.

The term "aryl group substituent" refers to a substituent chosen from halogen, CN, $CF_3$, $CH_2F$, and $NO_2$.

The term "benzofused" refers to the addition of a ring system sharing a common bond with the benzene ring.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "optionally substituted" means optionally substituted with one or more of the groups specified, at any available position or positions.

It will be appreciated that the AAA analogs according to the invention can contain one or more asymmetrically substituted carbon atoms (i.e., chiral centers). The presence of one or more of these asymmetric centers in an analog of the formulas shown in FIGS. 5–7 can give rise to stereoisomers, and in each case the invention is to be understood to extend to all such stereoisomers, including enantiomers and diastereomers, and mixtures including racemic mixtures thereof.

Isomers and analogs can be used according to the subject invention so long as the isomers or analogs exhibit the desired biological activity. Biological activity characteristics can be evaluated, for example, through the use of binding assays, or assays that measure cellular response.

An isomer or analog having the capability to modulate ionotropic glutamate receptor (iGluR) activity and/or metabotropic glutamate receptor (mGluR) activity would be considered to have the desired biological activity in accordance with the subject invention. For therapeutic applications, an isomer or analog of the subject invention preferably has the capability to inhibit ionotropic glutamate receptor (iGluR) activity and to modulate metabotropic glutamate receptor (mGluR) activity.

The subject invention brings new, safe, and highly effective treatments to the field of neuroprotective drugs. Specifically, naturally occurring aromatic amino acids (AAAs), including L-Tyrosine (L-Tyr), L-Phenylalanine (L-Phe), and L-Tryptophan (L-Trp), significantly and reversibly attenuate GluR-mediated miniature excitatory postsynaptic currents (mEPSCs) in hippocampal neurons. As demonstrated by the Examples described herein, the AAAs diminish control mEPSCs during normoxia and diminish mEPSCs which are augmented during ischemic insult (energy deprivation, ED).

The AAAs useful according to the subject invention serve as safe, highly effective, and reversible pharmacological tools to acutely and/or chronically treat many neurological disorders that involve excessive activation of iGluRs. The AAAs effectively inhibit GluR-mediated mESPCs during normoxia, as well as GluR-mediated mEPSCs, which are augmented during ischemic conditions (energy deprivation, ED). This effect of AAAs on GluR-mediated mEPSCs in cultured hippocampal neurons represents a cellular surrogate of the neuroprotective action of AAAs in a variety of neurological disorders.

According to the methods of the subject invention, an AAA is administered in an amount effective to increase the concentration of the AAA within the brain to a level above physiologically normal. For example, an AAA can be administered in an amount sufficient to bring the patient's AAA blood plasma level within the range of about 200 $\mu$M to about 2000 $\mu$M. Preferably, the patient's AAA blood plasma level is brought to within the range of about 300 $\mu$M to about 1800 $\mu$M. More preferably, the patient's AAA blood plasma level is brought to within the range of about 800 $\mu$M to about 1500 $\mu$M. However, the appropriate concentration of AAAs in the blood for neuroprotection can be adjusted, as the permeability of the blood-brain barrier can vary markedly with different disease states. In addition, the precise dosage will depend on a number of clinical factors, for example, the type of patient (e.g., human, non-human mammal, or other animal), age of the patient, and the condition under treatment and its severity. A person having ordinary skill in the art would readily be able to determine, without undue experimentation, the appropriate dosages required to achieve the appropriate levels.

In another embodiment, the methods of the subject invention comprise co-administering a facilitating substance that can enhance uptake of the AAA across the blood-brain barrier, thereby more efficiently raising the concentration of the AAA within the brain, and/or increases the activity of the AAA that is already present in the brain (e.g., endogenously or exogenously present). As used herein, the term "co-administering" means including the facilitating substance within a composition that also comprises the AAA, or separately administering the facilitating substance before, during, or after administration of the AAA. Examples of facilitating substances include, but are not limited to, agents that enhance AAA transport, enhance maximum activity or affinity for the AAA, and/or agents that promote binding of the AAA to receptors in neuronal tissue (e.g., allosteric enhancer).

A "patient" refers to a human, non-human mammal, or other animal in which modulation of an ionotropic glutamate receptor (iGluR) will have a beneficial effect. Patients in need of treatment involving modulation of iGluRs can be identified using standard techniques known to those in the medical profession.

The AAAs utilized in the subject invention can be obtained through a variety of methods known in the art. For example, the naturally occurring levorotatory forms of tyrosine, tryptophan, and phenylalanine can be produced by recombinant technology, as disclosed in U.S. Pat. No. 5,605,818. Methods for artificial synthesis of amino acids, isomers, and analogs are also known to those skilled in the art.

The AAAs utilized in the subject invention can be independent residues, or residues linked with other residues, which are either the same or different (e.g., a fusion protein or fusion peptide). For example, two or more residues can be linked by peptide bonds (forming a peptide), or hydrocarbon linkages appropriate for the AAAs. There may be, for example, two or more residues connected through at least one residue that is cleaved by an enzyme (e.g., a proteolytic enzyme). The enzyme can be endogenous to the patient, or exogenous to the patient and co-administered.

A further aspect of the present invention provides a method of modulating the activity of a glutamate receptor (e.g., a metabotropic or ionotropic glutamate receptor), and includes the step of contacting the receptor with an AAA that modulates one or more activities of the glutamate receptor, in general, either stimulating activity or inhibiting activity of the receptor. The method can be carried out in vivo or in vitro. The contacting step can be carried out with the receptor at various levels of isolation. For example, the AAA can be placed in contact with the receptor while the receptor is associated with tissue, the cell (e.g. neurons or glia), or fully isolated. The subject invention also provides methods for inhibiting GluR-mediated synaptic transmission between neurons and/or decreasing Glu concentration in the synaptic cleft by the administration of an AAA. These methods can be carried out in vivo or in vitro.

High blood concentrations of L-Phe (>1200 $\mu$M versus 55–60 $\mu$M in healthy patients) cause the neurological disease phenylketonuria (PKU) (Knox WE [1972] Stanbury J B et al., eds., $3^{rd}$ ed., McGraw Hill, New York, pp. 266–295; Scriver C R et al. [1989] Scriver et al., eds., McGraw-Hill, New York, pp. 495–546). Unless diagnosed and treated early in life with a L-Phe-restricted diet, irreversible brain damage occurs (Berry H K et al. [1979] Dev Med Child Neurol 21:311–320; Pennington B F et al. [1985] Am J Ment Defic 89:467–474). However, high concentrations of L-Phe are harmful only during the first years of life, and only during chronic exposure to elevated concentrations of this amino acid. Phenylketonuric patients typically discontinue their therapeutic special diet when they reach adulthood. All PKU-related studies converge on the same conclusion that after the age of 10 years, IQ development is stable for different degrees of dietary relaxation (Burgard P [2000] Eur J Pediatr 159 (Suppl 2): S74–S79). Thus, in one embodiment, the patient administered the AAA is greater than about ten years old.

While the AAA can be administered as an isolated compound, it is preferred to administer the AAA in the form of a pharmaceutical composition. The subject invention thus further provides pharmaceutical compositions comprising an AAA as an active ingredient, or physiologically acceptable salt(s) thereof, in association with at least one pharmaceutically acceptable carrier or diluent. The pharmaceutical composition can be adapted for various forms of parenteral administration, such as intravenous and nasal routes. Administration can be continuous or at distinct intervals as can be determined by a person skilled in the art.

The pharmaceutical compounds of the subject invention can be formulated according to known methods for preparing pharmaceutically useful compositions. Formulations are described in a number of sources which are well known and readily available to those skilled in the art. For example, *Remington's Pharmaceutical Sciencse* (Martin E W [1995] Easton Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The subject invention also provides an article of manufacture useful in treating a neurological condition characterized by overactivation of an ionotropic glutamatergic receptor. The article contains a pharmaceutical composition containing an AAA, and a pharmaceutically acceptable carrier or diluent. The article of manufacture can be, for example, an intravenous bag, a syringe, a nasal applicator, or a microdialysis probe. The article of manufacture can also include printed material disclosing instructions for the parenteral treatment of the neurological condition. The printed material can be embossed or imprinted on the article of manufacture and indicate the amount or concentration of the AAA, recommended doses for parenteral treatment of the neurological condition, or recommended weights of individuals to be treated.

All patents, patent applications, and publications referred to or cited herein are incorporated by reference in their entirety to the extent they are not inconsistent with the explicit teachings of this specification.

Materials and Methods

Cell preparation. Hippocampi were dissected from newborn rats and treated with 0.25% trypsin to dissociate cells, using the exact procedures that were employed for preparation of cortical cultures (Chandler L J et al. [1997] Mol Pharmacol 51: 733–40). Dissociated cells were resuspended in Neurobasal Medium containing B-27 serum-free supplement (Invitrogen Life Technologies, Carlsbad, Calif.), and were plated in poly-L-lysine coated 35 mm Nunc plastic tissue culture dishes ($1.5 \times 10^6$ cells/dish/2 ml media). Cells were cultured in an atmosphere of 5% $CO_2$/95% air, and 50% of the media was replaced every 3 days. Neurons were used for electrophysiological recordings 7 to 20 days after plating.

Electrophysiological recordings. Electrophysiological recordings of miniature excitatory postsynaptic currents (mEPSCs) in cultured rat hippocampal neurons were made in the whole cell configuration of the patch-clamp technique (Hamill O P et al. [1981] Pflugers Arch; 391: 85–1000) using an Axopatch 200B amplifier (Axon Instruments, Foster City, Calif.). Patch microelectrodes were pulled from 1.5 mm borosilicate glass tubing using a two-stage vertical pipette puller (Narishige, East Meadow, N.Y.). When filled with recording solution, patch microelectrodes had a resistance of 3–5 M. For rapid application of drug-containing solutions to neurons, the SF-77B system (Warner Instrument Corp., Hamden, Conn.) was used. Current data was digitized on-line using a DigiData 1200A analog-to-digital board and stored on the hard disc of an IBM compatible Pentium computer (GP7-600 MHz, Gateway Computer, Sioux City, N.D.). Voltage-clamp experimental protocols and off-line data analysis were performed using the software program pCLAMP7 (Axon Instruments) and Mini Analysis 5.2.7 software (Synaptosoft, Leonia, N.J.), respectively. The experiments were performed at room temperature (22–23° C.). Holding membrane potential was −60 mV.

Solution and drugs. The extracellular control solution contained (in mM): NaCl 140, $CaCl_2$ 2, KCl 4, HEPES 10, Glucose 11, Glycine 0.001, TTX 0.0005, strychnine 0.001, bicuculline methiodide 0.02. The pH of the extracellular solution was adjusted to 7.4 using NaOH. The solution for filling the patch electrodes contained (in mM): Cs gluconate 135, KCl 10, $MgCl_2$ 1, $CaCl_2$ 1, ethyleneglycoltetraacetic acid (EGTA) 11, TEA 2, $Na_2$ATP 2, $Na_2$GTP 0.2, HEPES 10. The pH of the intracellular solution was adjusted to 7.4 using CsOH. Various concentrations of L-Phe, L-Tyr, L-Trp, dizocilpine (MK-801; (+)-5-methyl-10,11-dihydroxy-5H-dibenzo(a,b)cyclohepten-5,10-imine) were added to the extracellular solution. All compounds were purchased from Sigma Chemical Co., St Louis, Mo.

Statistical data analysis. Values are reported as mean±SEM. Prior to parametric testing, the assumption of normality was validated using the Kolmogorov-Smirnov test with Lilliefor's correction (SSPS v10, SPSS, Inc., Chicago, Ill.). Multiple comparisons among groups were analyzed using ANOVA (two or one way repeated measures with 2 or 1 way replication where appropriate) followed by Student-Newman-Keuls testing. Single comparisons were analyzed using a 2-tailed Student's t test. A $P<0.05$ was considered significant.

Following are examples which illustrate procedures for practicing the invention. These examples should not be construed as limiting. All percentages are by weight and all solvent mixture proportions are by volume unless otherwise noted.

EXAMPLE 1

The Effect of Aromatic Amino Acids (AAAs) on Miniature Excitatory Postsynaptic Currents (mEPSCs) in Hippocampal Neurons Hippocampi were dissected from newborn rats and treated with trypsin to dissociate the cells. The hippocampal cells were then resuspended in Neurobasal Medium containing B-27 serum-free supplement, and cultured. Various concentrations of L-Phe, L-Tyr, L-Trp, dizocilpine (MK-801; (+)-5-methyl-10,11-dihydroxy-5H-dibenzo(a,b)cyclohepten-5,10-imine) were added to the extracellular solution. Electrophysiological recordings of miniature excitatory postsynaptic currents (mEPSCs) in cultured rat hippocampal neurons were made in the whole cell configuration. The current data was then digitized and analyzed.

FIGS. 1A–1C show the effect of L-Phe on mEPSCs in rat cultured hippocampal neurons. Examples of mEPSCs, recorded in the presence of the NMDA channel blocker MK801 (10 M) before, during, and after application of L-Phe (0.1 mM, 0.3 mM, 1 mM, and 3 mM) are shown in FIG. 1A. FIG. 1B shows an example of averaged mEPSCs (n=97 events in presence of 3 mM L-Phe; n=2230 events under control conditions) recorded from the same neuron shown in FIG. 1A. FIG. 1C shows the concentration-dependence of attenuation of the frequency of mEPSCs caused by L-Phe. The frequencies of mEPSCs were normalized to control values and plotted against the concentration of L-Phe. Data are expressed as mean±S.E.M. for 5 to 8 cells. *, P<0.01 compared to control. Curve fitting was made according to the 4-parameter logistic equation. Some error bars fell with the radius of a symbol. The concentration of glycine was 1 M whereas the membrane potential was –60 mV.

FIGS. 2A and 2B show the effect of L-tyrosine, L-phenylalanine, and L-tryptophan on mEPSCs in rat cultured hippocampal neurons. Examples of mEPSCs, recorded in the presence of the NMDA channel blocker MK-801 (10 M) before, during, and after application of L-tyrosine (L-Tyr), L-phenylalanine (L-Phe), or L-Tryptophan (L-Trp) (1000 M) are shown in FIG. 2A. FIG. 2B shows summary data for 5–8 experiments demonstrating the effect of L-Tyr, L-Trp and L-Phe on the frequency of mEPSCs. The frequencies of events were normalized to control values and plotted against the concentration of L-Tyr, L-Trp and L-Phe. The results are presented as mean±S.E.M. *, P<0.01 compared to control. The concentration of glycine was 1 M, whereas the membrane potential was 60 mV.

Figures 3A, 3B, 3C:
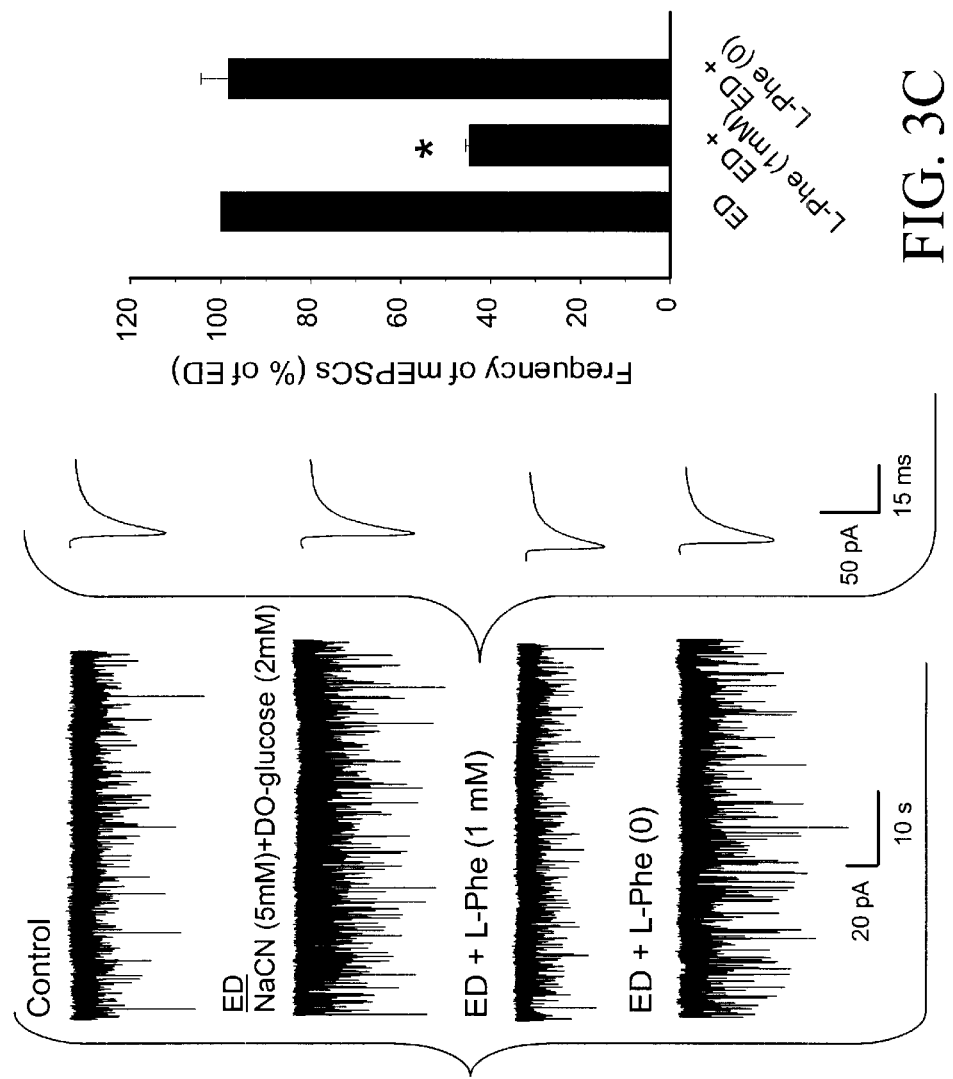
FIGS. 3A–3C show the effect of L-Phe on mEPSCs in rat cultured hippocampal neurons during energy deprivation (ED). To induce ED, glucose was replaced with 2-deoxyglucose, and sodium cyanide (NaCN) was added. Examples of mEPSCs, recorded in the presence of the NMDA channel blocker MK-801 in control, during ED, during ED in the presence of L-Phe, and during ED after washout of L-Phe are shown in FIG. 3A.

FIGS. 3A–3C show the effect of L-Phe on mEPSCs in rat cultured hippocampal neurons during energy deprivation (ED). To induce ED, glucose was replaced with 2 mM 2-deoxyglucose, and 5 mM sodium cyanide (NaCN) was added. Examples of mEPSCs, recorded in the presence of the NMDA channel blocker MK-801 (10 $\mu$M) in control, during ED, during ED in the presence of L-Phe (1000 $\mu$M), and during ED after washout of L-Phe are shown in FIG. 3A. FIG. 3B shows an example of averaged mEPSCs (n=973 events in presence of L-Phe; n=3331 events under control conditions) recorded from the same neuron shown in FIG. 3A. FIG. 3C shows summary data for four experiments demonstrating the effect of L-Phe on the frequency of mEPSCs. The frequency of mEPSCs during ED was taken as 100%.

Figures 4A, 4B:
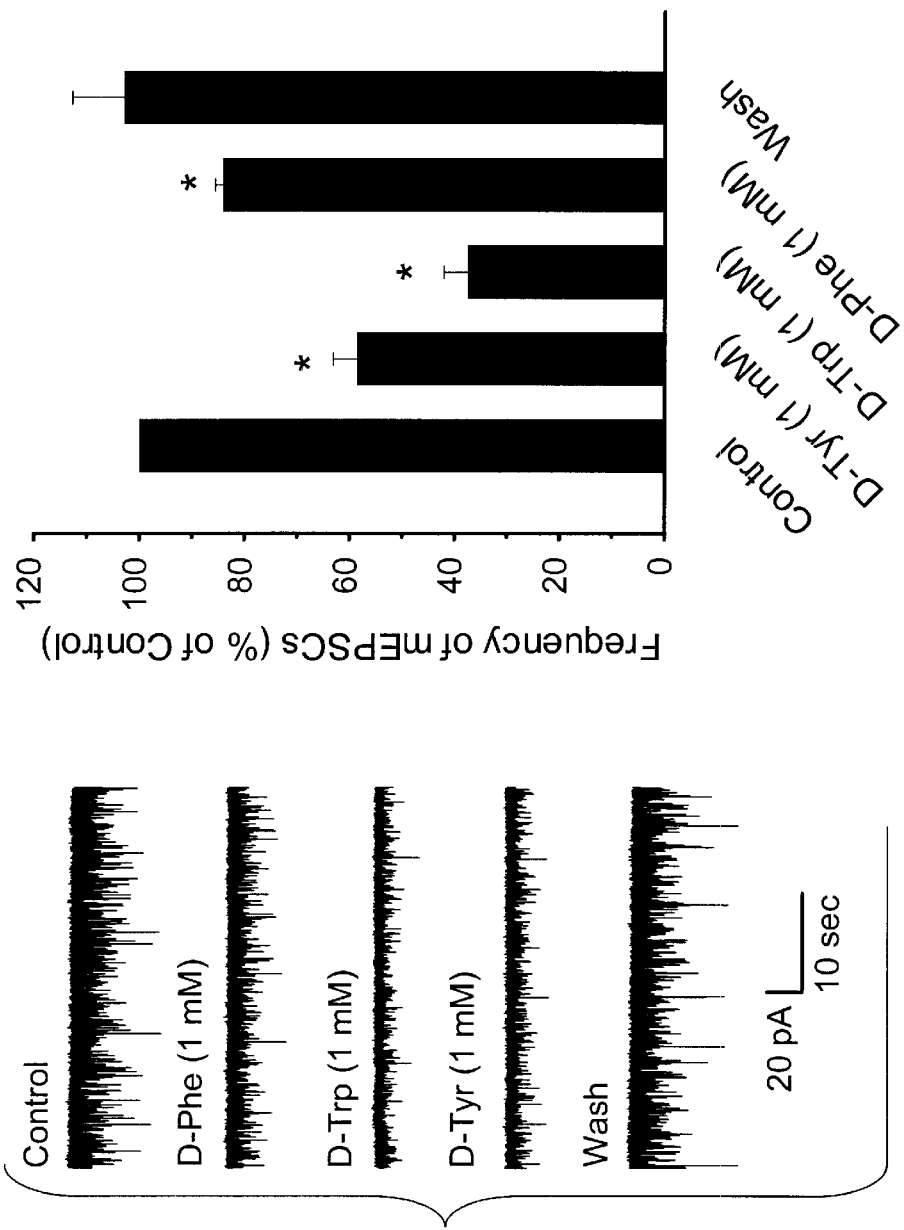
FIGS. 4A and 4B show the effect of D-tyrosine, D-tryptophan, and D-phenylalanine the frequency of mEPSCs in rat cultured hippocampal neurons. Examples of mEPSCs, recorded in the presence of the NMDA channel blocker MK-801 before, during, and after application of D-phenylalanine (D-Phe), D-tryptophan (D-Trp), and D-tyrosine (D-Tyr) are shown in FIG. 4A.

FIGS. 4A and 4B show the effect of D-tyrosine, D-tryptophan, and D-phenylalanine on the frequency of mEPSCs in rat cultured hippocampal neurons. Examples of mEPSCs, recorded in the presence of the NMDA channel blocker MK-801 before, during and after application of D-phenylalanine (D-Phe), D-tryptophan (D-Trp), and D-tyrosine (D-Tyr) are shown in FIG. 4A. FIG. 4B shows summary data for 5–8 experiments demonstrating the effect of D-Tyr, D-Trp, and D-Phe on the frequency of mEPSCs. The frequencies of mEPSCs were normalized to control values and plotted against the concentration of D-Tyr, D-Trp, and D-Pbe. The results are presented as mean±S.E.M. *, P<0.01 compared to control.

EXAMPLE 2

Evaluation of the Neuroprotective Effects of AAAs in Hippocampal Cell Cultures

Neurons will be subjected to oxygen glucose deprivation (OGD) at 14–16 days in vitro. Neurobasal medium (Gibco/Life Technologies, CA) will be removed and put aside. Glucose-free medium, warmed to 37° C., will be applied to the neurons. Cultures will then be placed into an airtight chamber (Billups-Rothenberg Inc., Del Mar, Calif.) flushed with 95% $N_2$/5% $CO_2$ until oxygen concentration fell to less than 1%. The chamber should be maintained at 37° C. for 1–2.5 hr, the original conditioned Neurobasal medium will be reapplied, with or without AAAs (1 mM) and will be returned to the incubator for the duration of the experiment.

Cell viability at different experimental conditions can be assessed by counting phase-bright cells (live cells) under phase-contrast microscopy and propidium iodide (PI)-labeled nuclei (dead cells) under fluorescence microscopy). Viability can be calculated as the ratio of phase-bright cells to total cells (i.e., phase-bright plus PI-stained) (R. Tremblay et al., 2000). The degree of the leakage of the enzyme lactate dehydrogenaze (LGH) will be used as criteria of the necrotic cell damages. The apoptotic-like features can be evaluated by using an enzyme-linked immunosorbent assay (ELISA) with anti-histone/DNA monoclonal antibodies as evidence for DNA damage, and by measuring the caspase activity in rat hippocampal cultures.

It should be understood that the examples and embodiments described herein are for illustrative purposes only and that various modifications or changes in light thereof will be suggested to persons skilled in the art and are to be included within the spirit and purview of this application.

We claim:

1. A method for treating a neurological condition characterized by excessive activation of glutamatergic ionotropic receptors, said method comprising parenterally administering to a patient suffering from the neurological condition at least one aromatic amino acid, isomer, or analog thereof, wherein the neurological condition is selected from the group consisting of ischemia, stroke, spinal cord injury, and traumatic brain injury.

2. The method according to claim 1, wherein the aromatic amino acid, isomer, or analog thereof, is administered to the patient intravenously.

3. The method according to claim 1, wherein the aromatic amino acid, isomer, or analog thereof, is administered to the patient intranasally.

4. The method according to claim 1, wherein the aromatic amino acid, isomer, or analog thereof, is administered in an amount sufficient to raise the concentration of the aromatic amino acid, isomer, or analog to above a physiologically normal level.

5. The method according to claim 1, wherein the aromatic amino acid, isomer, or analog thereof, is administered in an amount sufficient to raise the patient's blood plasma level of the aromatic amino acid, isomer, or analog, to within a range of about 200 $\mu$M to about 2000 $\mu$M.

6. The method according to claim 1, wherein the aromatic amino acid, isomer, or analog thereof, is administered in an amount sufficient to raise the patient's blood plasma level of the aromatic amino acid, isomer, or analog, to within a range of about 300 $\mu$M to about 1800 $\mu$M.

7. The method according to claim 1, wherein the aromatic amino acid, isomer, or analog thereof, is administered in an amount sufficient to raise the patient's blood plasma level of the aromatic amino acid, isomer, or analog, to within a range of about 800 $\mu$M to about 1500 $\mu$M.

8. The method according to claim 1, wherein the aromatic amino acid is selected from the group consisting of L-tyrosine, L-tryptophan, and L-phenylalanine.

9. The method according to claim 1, wherein a mixture of the aromatic amino acids are administered, and wherein the mixture is selected from the group consisting of: L-tyrosine and L-tryptophan; L-tyrosine and L-phenylalanine; L-tryptophan and L-phenylalanine; and L-tyrosine, L-tryptophan, and L-phenylalanine.

10. The method according to claim 1, wherein the aromatic amino acid isomer is an enantiomer selected from the group consisting of D-tyrosine, D-tryptophan, and D-phenylalanine.

11. The method according to claim 1, wherein a mixture of the aromatic amino acid isomers are administered, and wherein the mixture is selected from the group consisting of: D-tyrosine and D-tryptophan; D-tyrosine and D-phenylalanine; D-tryptophan and D-phenylalanine; and D-tyrosine, D-tryptophan, and D-phenylalanine.

12. The method according to claim 1, wherein a mixture of the aromatic amino acid and the isomer is administered, wherein the mixture comprises a levorotatory aromatic amino acid and a dextrorotatory aromatic amino acid.

13. The method according to claim 1, wherein a mixture of the aromatic amino acid and the isomer is administered, and the mixture comprises L-phenylalanine and D-phenylalanine.

14. A method for treating a neurological condition, said method comprising administering at least one aromatic amino acid, isomer, or analog thereof, to a patient in need of such treatment, wherein the neurological condition is selected from the group consisting of ischemia, stroke, spinal cord injury, and traumatic brain injury.

15. The method according to claims 14, wherein the aromatic amino acid, isomer, or analog thereof, is administered to the patient intravenously.

16. The method according to claim 14, wherein the aromatic amino acid, isomer, or analog thereof, is administered to the patient intranasally.

17. The method according to claim 14, wherein the aromatic amino acid, isomer, or analog thereof, is administered in an amount sufficient to raise the concentration of the aromatic amino acid, isomer, or analog to above a physiologically normal level.

18. The method according to claim 14, wherein the aromatic amino acid, isomer, or analog thereof, is administered in an amount sufficient to raise the patient's blood plasma level of the aromatic amino acid, isomer, or analog, to within a range of about 200 $\mu$M to about 2000 $\mu$M.

19. The method according to claim 14, wherein the aromatic amino acid, isomer, or analog thereof, is administered in an amount sufficient to raise the patient's blood plasma level of the aromatic amino acid, isomer, or analog, to within a range of about 300 $\mu$M to about 1800 $\mu$M.

20. The method according to claim 14, wherein the aromatic amino acid, isomer, or analog thereof, is administered in an amount sufficient to raise the patient's blood plasma level of the aromatic amino acid, isomer, or analog, to within a range of about 800 $\mu$M to about 1500 $\mu$M.

21. The method according to claim 14, wherein the aromatic amino acid is selected from the group consisting of L-tyrosine, L-tryptophan, and L-phenylalanine.

22. The method according to claim 14, wherein a mixture of the aromatic amino acids are administered, and wherein the mixture is selected from the group consisting of: L-tyrosine and L-tryptophan; L-tyrosine and L-phenylalanine; L-tryptophan and L-phenylalanine; and L-tyrosine, L-tryptophan, and L-phenylalanine.

23. The method according to claim 14, wherein the aromatic amino acid isomer is an enantiomer selected from the group consisting of D-tyrosine, D-tryptophan, and D-phenylalanine.

24. The method according to claim 14, wherein a mixture of the aromatic amino acid isomers are administered, and wherein the mixture is selected from the group consisting of: D-tyrosine and D-tryptophan; D-tyrosine and D-phenylalanine; D-tryptophan and D-phenylalanine; and D-tyrosine, D-tryptophan, and D-phenylalanine.

25. The method according to claim 14, wherein a mixture of the aromatic amino acid and the isomer is administered, wherein the mixture comprises a levorotatory aromatic amino acid and a dextrorotatory aromatic amino acid.

26. The method according to claim 14, wherein a mixture of the aromatic amino acid and the isomer is administered, and the mixture comprises L-phenylalanine and D-phenylalanine.

* * * * *

UNITED STATES PATENT AND TRADEMARK OFFICE
CERTIFICATE OF CORRECTION

PATENT NO. : 6,620,850 B2
DATED : September 16, 2003
INVENTOR(S) : Anatoly E. Martynyuk et al.

It is certified that error appears in the above-identified patent and that said Letters Patent is hereby corrected as shown below:

Title page,
Item [75], "Inventors: Anatoly E. Martynyuk, Gainesville, FL (US); Donn Michael Dennis, Gainesville, FL (US); Alexander V. Glushakov, Gainesville, FL (US); Colin Sumners, Gainesville, FL (US)" should read -- Inventors: Anatoly E. Martynyuk, Gainesville, FL (US); Donn Michael Dennis, Gainesville, FL (US); Alexander V. Glushakov, Gainesville, FL (US); Colin Sumners, Gainesville, FL (US); M. Ian Phillips, Gainesville, FL (US) --

Signed and Sealed this

Third Day of February, 2004

JON W. DUDAS
*Acting Director of the United States Patent and Trademark Office*